United States Patent [19]

Sherlock et al.

[11] 4,205,073

[45] May 27, 1980

[54] ANTI-DIARRHEAL ANILINO NICOTINIC ACIDS AND METHOD OF USING SAME

[75] Inventors: Margaret H. Sherlock, Bloomfield; James F. Long, Whippany, both of N.J.

[73] Assignee: Schering Corporation, Kenilworth, N.J.

[21] Appl. No.: 572,982

[22] Filed: Apr. 30, 1975

[51] Int. Cl.$^2$ .................. A61K 31/455; A61J 3/06; A61J 3/10

[52] U.S. Cl. .................. 424/266; 424/14; 424/21

[58] Field of Search .................. 424/266

[56] References Cited

U.S. PATENT DOCUMENTS

| | | |
|---|---|---|
| 3,223,717 | 12/1965 | Bowers et al. |
| 3,337,570 | 8/1967 | Sherlock et al. ........... 424/266 X |
| 3,642,841 | 2/1972 | Windholz et al. |
| 3,689,653 | 9/1972 | Sherlock et al. ........... 424/266 |
| 3,839,344 | 10/1974 | Sherlock ........... 424/266 |
| 3,891,761 | 6/1975 | Sherlock ........... 424/266 |

FOREIGN PATENT DOCUMENTS

| | | | |
|---|---|---|---|
| 1914005 | 4/1950 | Fed. Rep. of Germany ........... 424/266 |
| 43186 | 2/1971 | Finland ........... 424/266 |
| 6604123 | 11/1966 | Netherlands ........... 424/266 |

OTHER PUBLICATIONS

Kohei et al., Chem. Abs., 1971, vol. 75, p. 139274.

*Primary Examiner*—Dale R. Ore
*Attorney, Agent, or Firm*—Raymond A. McDonald

[57] ABSTRACT

This invention relates to compositions of matter useful as anti-diarrheal agents and to the method of controlling and treating diarrhea in warm blooded animals. The active anti-diarrheal agents are substituted anilino nicotinic acids, and salts thereof and ester and hydrazine derivatives of said acids.

11 Claims, No Drawings

ANTI-DIARRHEAL ANILINO NICOTINIC ACIDS AND METHOD OF USING SAME

It is an object of this invention to provide novel pharmaceutical compositions which will have the effect of controlling and treating diarrhea in warm blooded animals. It is another object of this invention to provide a novel method for the treatment and control of diarrhea in warm blooded animals. Other objects, will also become apparent to those skilled in the art in the light of the instant specification.

It has been found that the objects of this invention may be realized by providing a pharmaceutical composition comprising, as an essential active anti-diarrheal ingredient thereof, a therapeutically effective amount of a compound having the general structural formula:

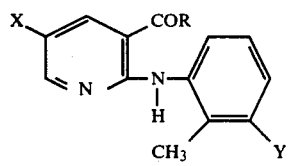

and the pharmaceutically acceptable salts thereof, wherein Y represents trifluoromethyl, difluoromethyl, or nitro, X represents hydrogen, chloro, bromo or hydroxy, and R represents —OH,-O-lower alkyl, O-CH$_2$CHOHCH$_2$OH,

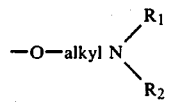

NHOH or NR$_1$NR$_2$, wherein R$_1$ and R$_2$ are each hydrogen or lower alkyl.

As used herein the term "lower alkyl", includes those straight and branched chain radicals having up to six carbon atoms, preferably methyl and ethyl. The preferred salt is the N-methyl glucamine salt and the preferred ester is the glyceryl ester.

The anilino nicotinic acids of this invention are prepared by condensing a 2-halo-5-X-nicotinic acid with the appropriate 2-methyl-3-Y-aniline; the condensation being effected by heating a mixture of at least equimolar quantities of the reactants. Preferably, the compounds are prepared by heating a 2-chloro-5-X-nicotinic acid or a 2-bromo-5-X-nicotinic acid with the appropriate 2-methyl-3-Y-aniline, said heating taking place in a high boiling solvent such as glycols (e.g. ethylene glycol, propylene glycol and the like) and aromatic hydrocarbons (e.g. xylene, phenol or cymene), or by merely melting an admixture of the reactants by the usual and standard techniques. In the melting procedure the reaction temperature will rise as the reaction proceeds. The reaction is completed generally after 10–15 minutes as evidenced by a fall in reaction temperature. The fused melt is then treated with aqueous base, e.g. sodium carbonate or sodium hydroxide, and extracted with a water immiscible solvent. The product, in the form of a soluble salt, is in the aqueous layer and is precipitated therefrom by acidifying with dilute mineral acid, filtered and recrystallized.

During the course of the reaction for each mole of reaction product there is formed a mole of hydrogen halide. Accordingly, it is preferred to employ 2 moles of the aniline for each mole of the 2-halo-5-X-substituted nicotinic acid. The extra mole of the former readily takes up the hydrogen halide formed in the form of an acid addition salt.

Alternatively, there may be employed an ester (lower alkyl) or the 2-halo-5-X-nicotinic acid. The ester group, if desired, may be subsequently hydrolyzed. (In some instances hydrolysis may occur during the reaction but the alcohol produced does not interfere with the desired condensation and is easily removed during isolation and purification.)

In addition to the use of the reactants in the above described nucleophillic displacement reaction, other equivalently functioning reactants may be employed to produce the desired novel composition of matter of this invention. For example, instead of employing a 2-halo-5-X-nicotinic acid, (or ester thereof), a 5-X-nicotinic acid (or ester thereof) having an alkoxy, alkylthio, methylsulfonyl or other equivalently functioning substituent in the 2-position thereof may be employed. In such instances the same reaction conditions used in the previously described nucleophillic displacement reaction would be employed. Alternatively, an N-substituted 2-methyl-3-Y-aniline reactant may be heated with the foregoing 2-substituted 5-X-nicotinic acids (or esters thereof) instead of employing the previously described 2-methyl-3-Y-anilines. Such equivalently functioning aniline reactants include those wherein a hydrogen atom attached to the nitrogen atoms has been replaced with substituents such as benzyl. Again in the use of these equivalently functioning reactants, the previously described nucleophillic displacement reaction conditions would be employed. In those instances wherein an N-substituted aniline reactant has been employed the 5-X-2-(N-substituted-2-methyl-3-Y-anilino) nicotinic acid (or ester thereof) may be subjected to standard procedures to remove the benzyl radical from the nitrogen atom. The preferred reactions may be summarized by the following schematic representation:

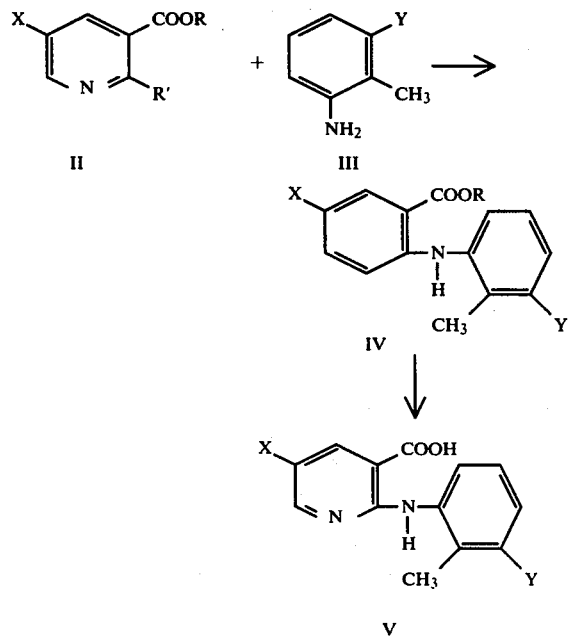

wherein R is hydrogen or lower alkyl, (or other derivatives readily, hydrolyzable to the free acid); R' is chloro, bromo, alkoxy, alkylthio, methylsulfonyl, nitro or other equivalently functioning substituent; X is hydrogen, hydroxy, chloro or bromo and Y is trifluoromethyl, difluoromethyl, or nitro.

Alternatively, the compounds embraced within this invention may also be prepared from the appropriate 2-amino nicotinic acid (or a readily hydrolyzable derivative thereof) by means of a nucleophillic displacement reaction with an appropriately O-phenyl halide according to standard techniques known in the art. Still another method for preparing those compounds having either a halogeno or nitro radical in the 5-position of the nicotinic acid moiety is by direct halogenation and nitration procedures effected upon the 2-(2-methyl-3-Y-anilino) nicotinic acids and derivatives thereof.

The glyceryl esters, lower alkanoyl esters, hydrazides, hydroxylamide, aminoalkyl esters, the tetrazole analogs, and other such derivatives may be prepared according to standard techniques already well known and taught in this art. Similarly, the alkali and the alkaline earth metal and amine salts of the compounds of this invention may be prepared by methods well known in the art. Representative of such salts are, in addition to sodium, those wherein the cation is ammonium, N-methyl glucamine, diethanolammonium, potassium, lithium, calcium, aluminum, and such other metals which advantageously allow for greater solubility or ease in formulation. Exemplary of the teachings by which the anilino nicotinic acids, their esters, salts and other derivatives may be prepared as U.S. Pat. Nos. 3,337,570, 3,839,344 and 3,478,040; said teachings being incorporated herein by reference.

The following examples are illustrative of the methods of synthesis of the tangible embodiments of this invention.

EXAMPLE 1

2-(2-Methyl-3-difluoromethylanilino) nicotinic acid

With stirring, reflux a mixture containing 5 g. of 2-chloronicotinic acid, 0.3 g. of p-toluene sulfonic acid, 12.5 g. of 2-methyl-3-difluoromethyl aniline, and 15 ml. of n-propanol for five hours. Treat the reaction mixture with ether and 6.2 g. of potassium hydroxide dissolved in 100 ml. of water. Separate and acidify the aqueous layer with dilute hydrochloric acid to yield the product 2-(2-methyl-3-difluoromethylanilino) nicotinic acid, m.p. 232°–234° after recrystallization from acetonitrile.

EXAMPLE 2

5-Bromo-2-(2-methyl-3-trifluoromethylanilino) nicotinic acid

Heat in an oil bath at 170° C. a mixture of 15 g. of 5-bromo-2-chloro-nicotinic acid, 12.2 g. of 2-methyl-3-trifluoromethyl aniline and 60 g. of phenol for three hours. Treat the resulting reaction mixture with ether and 5% sodium bicarbonate solution, concentrate and steam distil to obtain an oily residue. Dissolve the oily residue in dilute sodium hydroxide solution, acidify with dilute hydrochloric acid and filter. Recrystallize the product from methanol to yield 5-bromo-2-(2-methyl-3-trifluoromethylanilino) nicotinic acid, m.p. 222°–224° C.

EXAMPLE 3

5-Hydroxy-2-(2-methyl-3-trifluoromethylanilino) nicotinic acid

To a suspension of 10 g. of 2-(2-methyl-3-trifluoromethylanilino) nicotinic acid and 160 ml. of glacial acetic acid, add 9 ml. of 30% hydrogen peroxide solution at room temperature. Warm the reaction mixture on a steam bath for one hour and add an additional 5 ml. of 30% hydrogen peroxide. Heat the resulting mixture for three hours on a steam bath, dilute with water and filter. After recrystallization from acetic acid, the product, 5-hydroxy-2-(2-methyl-3-trifluoromethylanilino) nicotinic acid melts at 305°–308° (dec.)

EXAMPLE 4

2-(2'-Methyl-3'-trifluoromethylanilino) nicotinic acid

To 20 g. of 2-methyl-3-trifluoromethyl aniline heated at 200°, add, in a dropwise fashion, 11 g. of ethyl 2-chloro-nicotinate. Heat the reaction mixture at 200° for one-half hour, cool, pour the mixture onto ice and extract with ether. Concentrate the ether extracts, dry and fractionate the residue in vacuo; b.p. 143°–146°/0.15 mm; m.p. 44°–46°.

To a solution of 12 g. of ethyl 2-(2'-methyl-3'-trifluoromethylanilino) nicotinate in 100 ml. of methanol and 4.6 g. of potassium hydroxide in 10 ml. of water. Reflux the solution for three hours, concentrate in vacuo and dissolve the residue in water. Acidify the aqueous solution to yield the desired 2-(2'-methyl-3'-trifluoromethylanilino) nicotinic acid, m.p. 226°–228° C. after recrystallization from acetone-hexane.

By following the teachings of the foregoing examples as well as by the teachings of the above cited reference, there may also be produced the following nicotinic acids:

5-bromo-2-(2-methyl-3-difluoromethylanilino) nicotinic acid,
5-bromo-2-(2-methyl-3-nitroanilino) nicotinic acid,
5-chloro-2-(2-methyl-3-trifluoromethylanilino) nicotinic acid, and
5-hydroxy-2-(2-methyl-3-difluoromethylanilino) nicotinic acid.

By following the teachings of U.S. Pat. No. 3,478,040 the lower alkanoyl esters, the reactive ester intermediates (e.g. the cyanomethyl esters) the cyclic acetal intermediates (e.g. the β-γ-isopropylidenedioxypropyl esters) and the glyceryl esters of the foregoing sepcifically mentioned products, as well as for those other compounds embraced by formula I above may be prepared. Similarly, by following the teachings of U.S. Pat. No. 3,839,344 the N-methyl-D-glucamine salt of the acids embraced by formula I may also be prepared.

EXAMPLE 5

2-(2-Methyl-3-trifluoromethylanilino) nicotinic acid hydrazide

Heat, at reflux temperature, a solution of 6 g. of methyl 2(2-methyl-3-trifluoromethylanilino) nicotinate and 15 g. of hydrazine hydrate for three hours. Concentrate the reaction mixture to dryness, treat with water, filter and recrystallize the product from acetonitrile to yield the hydrazide, m.p. 178°–179°. The N-(2-methyl) hydrazide, m.p. 116°–118° C. (acetonitrile) and the N-(1-methyl) hydrazide, m.p. 104°–106° C. (ether-hexane) may also be prepared according to the same general method. Other alkyl hydrazides may similarly be prepared, as well as the hydrazides of the other nicotinic acids of formula I.

As stated above, the method for treating and controlling acute and chronic diarrheal conditions in warm blooded animals characterized by the secretion of water and electrolytes by the small intestine is effected by administering a therapeutically effective quantity of an anilino nicotinic acid of the structural formula I above, including the salts, esters and other derivatives (i.e. those which are readily hydrolyzable back to the free acid), which have been described hereinabove. The therapeutically effective quantity of a compound of this invention may readily be ascertained by standard and well-known techniques in the art. In testing for the anti-diarrheal activity the compounds are first tested in the rat castor oil/diarrhea model (i.e. the test wherein castor oil is the diarrhea-causing agent). Anti-diarrheal activity is then confirmed by measuring the anti-secretory activity in more sophisticated procedures such as cholera toxin and ricinoleic acid/bile salt-challenged secretion in intestinal loops of dogs.

Accordingly, from the foregoing test procedures, as well as by other standard laboratory techniques, as well as by comparison with well-known anti-diarrheal compositions, it has been found that the compounds of this invention reduce the water/electrolyte secretion, are non-constipating and exhibit a reasonable separation between therapeutic and untoward sideeffect doses. Thus, from these tests a therapeutically effective dosage range for the compounds of this invention is from 0.1 mg/kg. to about 40 mg/kg. of body weight. Although it is expected that a therapeutically effective dosage may be administered once a day, dosaging may take place three times daily. Of course, the actual total daily dosage will depend upon the severity of the diarrheal condition, its cause and other health factors of the animal being treated. Thus, in each instance the attending diagnostician will determine the dosage frequency and strength. In practice, the anti-diarrheal compounds of this invention may be administered orally and parenterally; intravenous administration being effective in some extremely severe and acute conditions, such as in the treatment of colitis in equines and bovines.

In their effect in reversing fluid and electrolyte secretion it is expected that not only will the compounds of this invention control and treat "simple" diarrhea but also that the compounds will be effective in treating diarrhea caused by cholera and other bacterial infestations (e.g. *Escherichia coli*), as well as the treatment and control of diarrhea caused by androgenous intestinal secretogauges (e.g. certain gastrointestinal hormones). Indeed, although cholera is somewhat self-limiting and cure depends upon fluid replacement, a drug treatment (such as by the compounds of this invention) aimed at inhibiting secretion would be invaluable in the practical management of large numbers of cholera victims in an underdeveloped environment.

Additionally, of specific value is the use of the compounds of this invention in veterinary medicine. For example, scours in piglets may be controlled by the administration of the compounds of this invention. Also the compounds find value in the treatment of colitis in horses, and cows, particularly when they have been inflicted with Colitis X. In such instances a very effective dosage is 1 mg/kg. of body weight administered intravenously as quickly after the first symptoms of colitis appears.

The anti-diarrheal agents of this invention can be administered as such, or can be administered in the form of a composition comprising the active ingredient and any of the commonly used pharmaceutical carriers. These carriers must be compatible with the active ingredient, and can be either solid or liquid, therapeutically active or inert. By using such carriers, one can make these compositions in the form of tablets, capsules, powders, oral suspensions, or syrups. The compositions can also be made in the form of sterile solutions which are suitable for injection. The compositions will contain from 1% to 95% by weight of active compound, and from 5% to 99% by weight of a suitable pharmaceutical carrier. These ranges, however, are not critical and can be varied as desired according to the circumstances.

A sterile solution suitable for injection is prepared by admixing from 0.5 to 5 parts by weight of the active ingredient, preferably in the form of its N-methyl-D-glucamine salt, and from 95 to 99.5 parts by weight of water or isotonic saline solution at a temperature and for time sufficient to dissolve the active ingredient. This solution is then sterilized by filtration or by the application of heat. The solution is preferably sterilized in an autoclave at a steam pressure of 15 pounds per square inch for from 5 to 15 minutes. A preferred solution for injection also contains preservatives such as a mixture of methyl- and propylparaben benzoic acid, or other nontoxic antimicrobial agents.

These injectable solutions can be prepared with a high concentration of active ingredient. The solution is then diluted to a desired concentration before it is used.

The compounds of Formula I can also be administered in the form of hard or soft gelatin capsules. These capsules are filled with the proper amount of active ingredient and a solid filler, such as starch, gelatin, lactose, talc, stearic acid, or magnesium stearate. Such a capsule can contain from 50 to 250 milligrams of active material, thus providing a minimum dose of active ingredient in a form convenient for oral administration.

The compounds of Formula I, when mixed with a suitable carrier, can also be formulated as tablets. Such carriers must be compatible with the active ingredient and can be the carriers mentioned for use with capsules, or can be such binders or fillers as cornstarch, acacia, gelatin, or cellulosic materials. Generally, any of the tableting materials conventionally used in pharmaceutical practice can be employed if there is no incompatibility with the active ingredient.

The tablets are made by admixing the active ingredient, a suitable filler, a lubricant or mold-release agent, and a binder, and compressing the mixture in a conventional tableting machine into tablets of a preselected size. Preferably, each tablet will contain from 50 to 250 milligrams of active ingredient. The tablets can be scored so that they are easily broken. Optionally, the tablets can be coated with tablet-coating materials, in order to make them more attractive and palatable. They can also have enteric coatings so that they will release their ingredients slowly and over a longer period.

The compounds of Formula I can also be formulated and administered as suspensions or syrups. The anti-diarrheal compound is usually present in such suspensions and syrups in amounts of from 1% to 5% by weight, however, lower or higher concentrations can be used.

The pharmaceutical carrier in such suspensions or syrups can be an aqueous vehicle such as an aromatic water, a syrup, or a pharmaceutical mucilage. Suitable aromatic waters include the following: Anise Water, N.F. (IX); Bitter Almond Water, N.F. (VIII); Camphor Water, N.F.; Cinnamon Water, U.S.P.; Fennel Water, N.F.; Peppermint Water, U.S.P.; Spearmint Water, N.F. (IX); Wintergreen Water, N.F. (IX). Suitable syrups include the following: Syrup (Simple Syrup), U.S.P.; Acacia Syrup, U.S.P.; Aromatic Eriodictyon Syrup, N.F.; Aromatic Rhubarb Syrup, N.F. (IX); Cacao Syrup, U.S.P.; Cherry Syrup, U.S.P.; Cinnamon Syrup, N.F. (IX); Citric Acid Syrup, U.S.P.; Compound Sarsparilla Syrup, N.F.; Compound White Pine Syrup, N.F.; Ginger Syrup, N.F. (IX); Glycyrrhiza (Licorice) Syrup, U.S.P.; Orange Syrup U.S.P.; Orange Flower Syrup, N.F.; Raspberry Syrup, U.S.P.; Rhubarb Syrup, N.F. (IX); Tolu Balsam Syrup, U.S.P.; Wild Cherry Syrup, U.S.P. Suitable pharmaceutical mucilages include the following: Acacia (Gum Arabic), U.S.P.; Acacia Mucilage, U.S.P.; Tragacanth, U.S.P.; Tragacanth Mucilage, N.F. The pharmaceutical carrier in the suspensions or syrups can also be a hydroalcoholic vehicle, such as an elixir. Suitable elixirs include the following: Aromatic Elixir, U.S.P.; Red Aromatic Elixir, N.F.; Glycyrrhiza Elixir, N.F.; Iso-Alcoholic Elixir (Iso-Elixir), N.F. Coloring agents, tinctures, spirits and other adjuvants can be admixed with the composition if desired.

Typical formulations incorporating the anti-diarrheal agents of Formula I are described below. These formulations are intended to be illustrative merely and no limitation is implied or intended.

TABLET FORMULATION

| Formula: | Grams per 1000 Tablets |
|---|---|
| 2-(2'-Methyl-3'-trifluoromethylanilino) nicotinic acid | 200.0 |
| Lactose | 90.0 |
| Dicalcium phosphate, hydrous | 122.5 |
| Polyvinylpyrrolidone | 25.0 |
| Polyvinylglycol 1500 | 7.5 |
| Corn Starch | 50.0 |
| Magnesium stearate | 5.0 |
| | 500.0 |

Mix the 2-(2'-methyl-3'-trifluoromethylanilino) nicotinic acid, the lactose and the dicalcium phosphate. Dissolve the polyethylene glycol 1500 and the polyvinylpyrrolidone in approximately 20 ml. of water. Granulate the powder blend with the water solution, adding additional water, if necessary, to produce a damp mass. Pass the wet granulation through a 12 mesh screen; spread on trays and air dry at 35° C. Blend the dry granules with the starch and the magnesium stearate. Compress into 500 mg. tablets.

CAPSULE FORMULATION

| Formula: | Grams per 1000 Capsules |
|---|---|
| 2-(2'-Methyl-3'-trifluoromethylanilino) nicotinic acid | 200.0 |
| Lactose | 198.0 |
| Magnesium stearate | 2.0 |
| | 400.0 |

Blend the ingredients and fill into hard gelatin capsules.

ELIXIR FORMULATION

| Formula: | | |
|---|---|---|
| 2-(2'-Methyl-3'-trifluoromethylanilino) nicotinic acid N-methyl-glucamine salt | grams per 1000 liters | 40.0 |
| Sugar | " | 500.0 |
| Glycerin | " | 200.0 |
| Compound orange spirit | grams per 1000 ml. | 10.0 |
| Alcohol | " | 100.0 |
| Amaranth | " | 0.1 |
| Water, q.s. 1000.0 ml. | | |

Dissolve the 2-(2'-methyl-3'-trifluoromethylanilino) nicotinic acid in the form of its N-methyl-D-glucamine salt, the sugar, the glycerin and the amaranth successively in approximately 400 ml. of water with the aid of heat. Cool the solution to room temperature. Dissolve the compound orange spirit in the alcohol and add the alcoholic solution to the elixir base. Add sufficient water to make the product measure 1000 ml. and agitate until homogeneous. Clarify the elixir by passing it through an asbestos pad, using a filter aid, if necessary.

INJECTION FORMULATION

| Formula: | Grams per 1000 ampuls |
|---|---|
| 2-(2'-Methyl-3'-trifluoromethylanilino) nicotinic acid, micronized | 110.0 |
| Water for injection, q.s. 1100.0 ml. | |

Dissolve the 2-(2'-methyl-3'-trifluoromethylanilino) nicotinic acid in the form of its N-methyl-D-glucamine salt in the water for injection. Pass the solution through a sterile 0.45 micron membrane filter. Fill aseptically into ampuls (1.1 ml. per ampul). Autoclave the sealed ampuls for 30 minutes under 20 p.s.i.g. steam pressure.

TABLET FORMULATION (I) Formula and method of manufacture of glyceryl 2-(2'-methyl-3'-trifluoromethylanilino) nicotinate. Enteric coated tablets

| Formula: | Mg/core |
|---|---|
| Glyceryl-2-(2'-methyl-3'-trifluoromethylanilino) nicotinate | 100.0 |
| Citric acid | 1.0 |
| Lactose, U.S.P. | 33.5 |
| Dicalcium phosphate | 70.0 |
| Pluronic F-68 | 30.0 |
| Sodium lauryl sulfate | 15.0 |
| Polyvinylpyrrolidone | 15.0 |
| Carbowax 1500 | 4.5 |
| Carbowax 6000 | 45.0 |
| 3A alcohol, 50 ml./1000 cores. | |
| Corn starch | 30.0 |
| Dry: | |
| Sodium lauryl sulfate | 3.0 |

TABLET FORMULATION continued (I) Formula and method of manufacture of glyceryl 2-(2'-methyl-3'-trifluoromethylanilino) nicotinate. Enteric coated tablets

| Formula: | Mg/core |
|---|---|
| Magnesium stearate | 3.0 |
| Tablet weight | 350.0 |

Procedure

The glyceryl 2(2'-methyl-3'-trifluoromethylanilino) nicotinate is mixed with the citric acid, lactose, dicalcium, phosphate, pluronic and sodium lauryl sulfate. The above mixture is screened through a No. 60 screen and damp granulated with an alcoholic solution consisting of polyvinylpyrrolidone, carbowax 1500 and 6000. Add additional alcohol, if necessary, to bring powders to a pasty mass. Add corn starch and continue mixing until uniform granules are formed. Pass through a No. 10 screen, tray and dry in oven at 100° C. for 12–14 hours. Reduce dried granulation through a No. 16 screen add sodium lauryl sulfate and magnesium sulfate, mix and compress into desired shape on a tablet machine.

Pluronic F-68 is a U.S. registered trademark for a non-ionic surface-active agent prepared by the addition of ethylene oxide to a polypropylene glycol which has a molecular weight of 1750.

Coating

The above cores are treated with a lacquer and dusted with talc to prevent moisture adsorption. Sub-coat layers are added to round out the core. A sufficient number of laquer coats are applied to make the core enteric. Additional sub-coats and smoothing coats are applied to completely round out and smooth the tablet. Color coats are applied until desired shade is obtained. After drying the coated tablets are polished to give the tablets an even gloss.

| (II) Capsule Formulations | |
|---|---|
| Formula: | Mg./Capsule |
| Glyceryl-2(2'-methyl-3'-trifluoromethylanilino) nicotinate, micronized | 100.00 |
| Citric acid | 1.00 |
| Pluronic, F-68 | 40.00 |
| Sodium lauryl sulfate | 20.00 |
| Lactose | 238.00 |
| Magnesium stearate | 101.00 |
| | 500.00 |

Procedure

Mix together glyceryl-2(2'-methyl-3'-trifluoromethylanilino)nicotinate, citric acid, pluronic, sodium lauryl sulfate and lactose. Pass through a No. 80 screen. Add magnesium stearate, mix and encapsulate into the proper size 2 piece gelatin capsule.

| (III) Oral Suspension |
|---|
| Formula: |
| Glyceryl-2(2'-methyl-3'-trifluoromethylanilino) nicotinate micronized - 100.0 mg./5 ml. |
| veegum, vanderbilt - 50.0 mg./5 ml. |
| Standard granulated sugar, U.S.P. - 2500.0 mg./5 ml. |
| Sorbitol solution, U.S.P. - 1250.0 mg./5 ml. |
| Sodium saccharin, NF - 50.0 mg./5 ml. |

| (III) Oral Suspension continued |
|---|
| Formula: |
| Sodium benzoate, U.S.P. - 5.0 mg./5 ml. |
| Ethanol, U.S.P. - 0.025 ml. |
| Menthol, U.S.P. - 1.000 mg./5 ml. |
| Flavor q.s. |
| Purified Water, U.S.P., to make 5 ml. |

Method of Preparation

Dissolve the sodium saccharin, sodium benzoate, standard granulated sugar and sorbitol solution in approximately 80% of the required amount of water. Disperse the Veegum in approximately 5% of the required amount of water and add the dispersion to the previously prepared syrup. Prepare a slurry of the glyceryl N-(2-methyl-3'-trifluoromethylanilino) nicotinate with approximately 10% of the required amount of water and pass through a suitable colloid mill until free of grittiness. Add the milled active slurry to the batch. Dissolve the menthol and flavor in the alcohol and add the resulting solution to the batch. Add sufficient purified water to bring the batch to total volume. Agitate until uniform.

If desired, the compounds may also be co-administered with other previously utilized anti-diarrheal compositions (e.g. polycarbophyl) although use of such other compositions is not necessary, the compounds of this invention being very effective in their anti-diarrheal use.

As is true for most classes of compounds useful in the treatment of physiological disorders, not all members are equipotent. From the above described laboratory techniques utilized in determining the anti-diarrheal activity of the compounds of this invention, it is determined that, in general, those anilino nicotinic acids, having the Y-substituent representative of trifluoromethyl or difluoromethyl are particularly useful and those having a 5-position-X-substituent representative of hydrogen or bromo are particularly effective. Particularly effective are those compounds when they are administered in the form of their glyceryl ester or in the form of their N-methyl glucamine salt. Specifically preferred compounds are 2-(2'-methyl-3'-trifluoromethylanilino) nicotinic acid, glyceryl ester of 2-(2'-methyl-3'-trifluoromethylanilino) nicotinic acid, the N-methylglucamine salt of 2-(2'-methyl-3'-trifluoromethylanilino) nicotinic acid, 5-bromo-2-(2-methyl-3-trifluoromethylanilino) nicotinic acid, 2-(2-methyl-3-difluoromethylanilino) nicotinic acid and 5-bromo-2-(2-methyl-3-difluoromethylanilino) nicotinic acid, 2-(2-methyl-3-trifluoromethylanilino) nicotinic acid hydrazide, 2-(2'-methyl-3'-trifluoromethylanilino)nicotinic acid, 2-methylhydrazide, and 2-(2'-methyl-3'-trifluoromethylanilino)-nicotinic acid 1-methylhydrazide.

We claim:

1. The method for the treatment and control of diarrhea which comprises administering to a mammal suffering from diarrhea a therapeutically effective quantity of an anilino nicotinic acid of the formula:

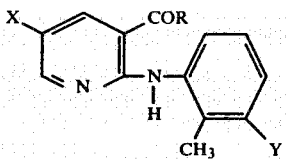

and the pharmaceutically acceptable salts thereof, wherein Y represents trifluoromethyl, difluoromethyl, or nitro, X represents hydrogen, halogeno, or hydroxy, and R represents OH, —O-lower alkyl, O—$CH_2$CHOH$CH_2$OH, O-alkyl-$NR_1R_2$, NHOH or $NR_1NR_2$, wherein $R_1$ and $R_2$ are each hydrogen or lower alkyl.

2. The method of claim 1, wherein R is OH.

3. The method of claim 1, wherein the pharmaceutical salt is the N-methyl-D-glucamine salt.

4. The method of claim 1, wherein the ester is glyceryl.

5. The method of claim 1 wherein X is hydrogen, Y is trifluoromethyl and R is O-$CH_2$CHOH$CH_2$OH, said compound being glyceryl 2-(2-methyl-3-trifluoromethylanilino) nicotinate.

6. The method of claim 1 wherein X is hydrogen, Y is trifluoromethyl and R is OH, said compound being 2-(2'-methyl-3'-trifluoromethylanilino) nicotinic acid.

7. The method of claim 1 wherein X is hydrogen, Y is difluoromethyl and R is OH, said compound being 2-(2-methyl-3-difluoromethylanilino) nicotinic acid.

8. The method of claim 1 wherein R represents a hydrazide.

9. The method according to claim 1 for the treatment and control of diarrhea in horses, wherein the condition is caused by an infection by Colitis X.

10. The method according to claim 1 for the treatment and control of diarrhea wherein the diarrhea has been caused by cholera.

11. The method according to claim 1 for the treatment and control of diarrhea in piglets, wherein the diarrhea is caused by the condition known as scours.

* * * * *